US00PP28080P3

(12) United States Plant Patent
Thompson et al.

(10) Patent No.: US PP28,080 P3
(45) Date of Patent: Jun. 6, 2017

(54) RASPBERRY PLANT NAMED 'PACIFIC GEMA'

(50) Latin Name: ***Rubus idaeus* L.**
Varietal Denomination: Pacific Gema

(71) Applicants: Ellen Thompson, Watsonville, CA (US); John Reuben Clark, Fayetteville, AR (US)

(72) Inventors: Ellen Thompson, Watsonville, CA (US); John Reuben Clark, Fayetteville, AR (US)

(73) Assignee: Pacific Berry Breeding, LLC, Salinas, CA (US)

( * ) Notice: Subject to any disclaimer, the term of this patent is extended or adjusted under 35 U.S.C. 154(b) by 9 days.

(21) Appl. No.: 14/544,823

(22) Filed: Feb. 24, 2015

(65) Prior Publication Data

US 2016/0249506 P1 Aug. 25, 2016

(51) Int. Cl.
*A01H 5/08* (2006.01)

(52) U.S. Cl.
USPC ..... Plt./204

(58) Field of Classification Search
USPC ..... Plt./156, 203, 204
See application file for complete search history.

(56) References Cited

U.S. PATENT DOCUMENTS

| | | | |
|---|---|---|---|
| PP19,512 | P3 | 12/2008 | Hauenstein |
| PP21,074 | P2 | 6/2010 | Aguas et al. |
| PP23,593 | P3 | 5/2013 | Banados et al. |

*Primary Examiner* — Susan McCormick Ewoldt
*Assistant Examiner* — Karen Redden
(74) *Attorney, Agent, or Firm* — King IP Law; Joshua King

(57) ABSTRACT

A new and distinct cultivar of Raspberry plant named 'Pacific Gema' as described and shown herein. 'Pacific Gema' provides balanced heavy crop loads on both primocanes and floricanes, large conic fruits that are flavorful and aromatic, high vigor and strong field tolerance to Raspberry Bushy Dwarf Virus (RBDV).

5 Drawing Sheets

Latin name of the genus and species of the plant claimed: *Rubus idaeus* L.

Variety denomination: 'PACIFIC GEMA'.

BACKGROUND AND SUMMARY

The new primocane-fruiting raspberry cultivar designated 'Pacific Gema' is shown herein. Botanically known as *Rubus idaeus* L., 'Pacific Gema' is a primocane-fruiting raspberry resulting from a hand-pollinated cross of female parent 'Pacific Deluxe' (U.S. Plant Pat. No. 21,074), a previous release from the same program, and the unpatented male parent '414a'. Pollination occurred in April 2008 and seeds from this controlled cross were subsequently harvested, cleaned, germinated, and field-established as seedlings in spring 2009 in Santa Cruz County, Calif.

'Pacific Gema' was first identified in the aforementioned seedling field in May 2010 in Watsonville, Calif. This variety was first propagated asexually by crown division in autumn 2010 in Watsonville, Calif. USA. The crown on the original plant was dug and parted into basal cane pieces (approximately 15 cm long) with root attached and replanted into a selection plot elsewhere on the farm, resulting in a 3-fold increase in plant material. Harvest and postharvest data were collected from this larger plot of 'Pacific Gema' throughout 2011, In January 2012, two actively growing etiolated shoots that were forced from roots in a greenhouse were sent to Lafayette, Oreg., USA, where vegetative material was explanted and established in vitro for micropropagation. Subsequent asexual propagation was done on-site in Watsonville, Calif. and, along with tissue-cultured plantlets, 'Pacific Gema' was evaluated extensively over the next several years for performance and genetic stability.

The present cultivar, 'Pacific Gema' offers many advantages over the existing, patented cultivar and maternal parent, 'Pacific Deluxe' (U.S. Plant Pat. No. 21,074) in that the root and subsequent cane vigor is significantly greater, floricane budbreak is more uniform, average fruit size is larger and more conic in shape. The increased vigor offers advantages in propagation, particularly in a nursery setting where roots are produced for sale to commercial growers. The improved floricane budbreak provides growers with a more reliable spring crop. The larger berries help growers fill baskets more quickly, leading to increased harvest efficiency.

A second example of an existing, patented cultivar is 'Pacific Majesty', U.S. Plant Pat. No. 23,593, another previous release from the same program. The present cultivar, 'Pacific Gema' has superior flavor/aroma and higher field tolerance of Raspberry Bushy Dwarf Virus (RBDV) compared with 'Pacific Majesty'.

A third example of an existing, patented cultivar is 'Rafzaqu', U.S. Plant Pat. No. 19,512 (aka Himbo Top®). The present cultivar, 'Pacific Gema' has firmer fruit and more berries per inflorescense compared with 'Rafzaqu', though both are of similar height.

Thus, these characteristics help define 'Pacific Gema' as a new and distinct cultivar of primocane-fruiting raspberry. 'Pacific Gema' may be recognized by its high vigor, uniform floricane budbreak, tall canes which are architecturally laden with conic berries and which consistently taste sweet and have a glossy appearance

BRIEF DESCRIPTION OF THE PHOTOGRAPHS

DETAILED DESCRIPTION

Figure 1:
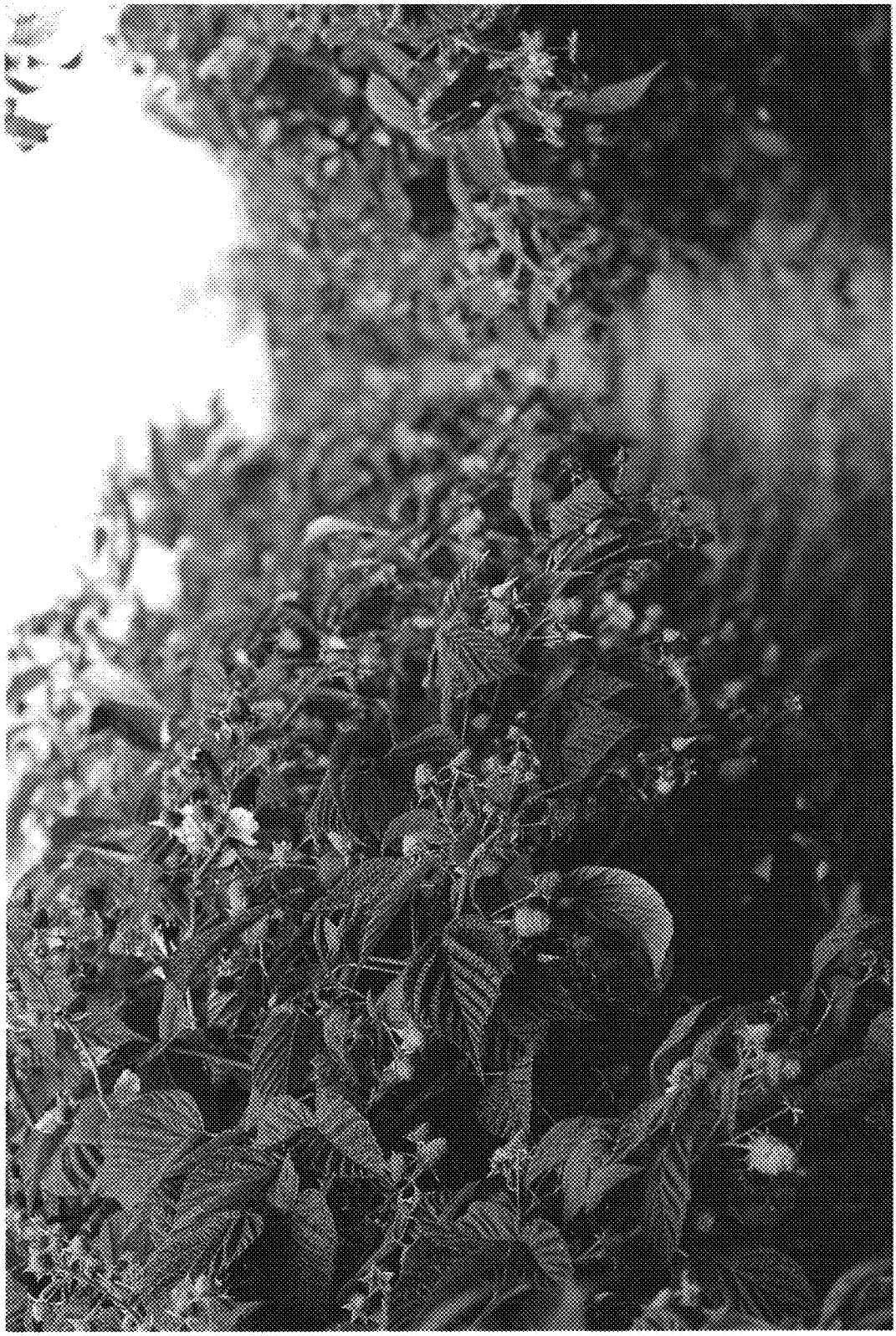
FIG. 1 is a photograph showing the canopy of the Raspberry cultivar 'Pacific Gema'.
Figure 2:
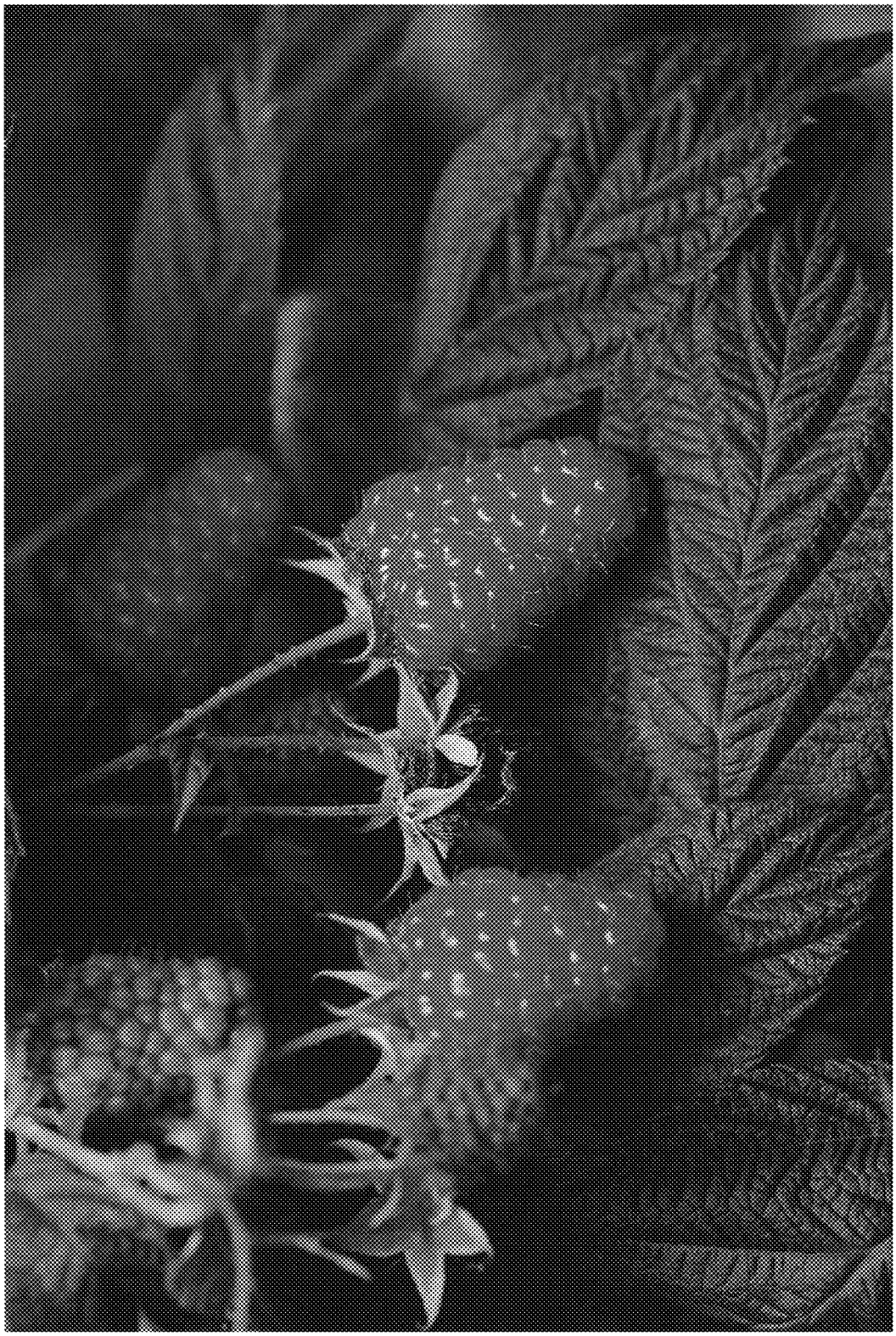
FIG. 2 is a further photograph showing the canopy of the Raspberry cultivar 'Pacific Gema'.
Figure 3:
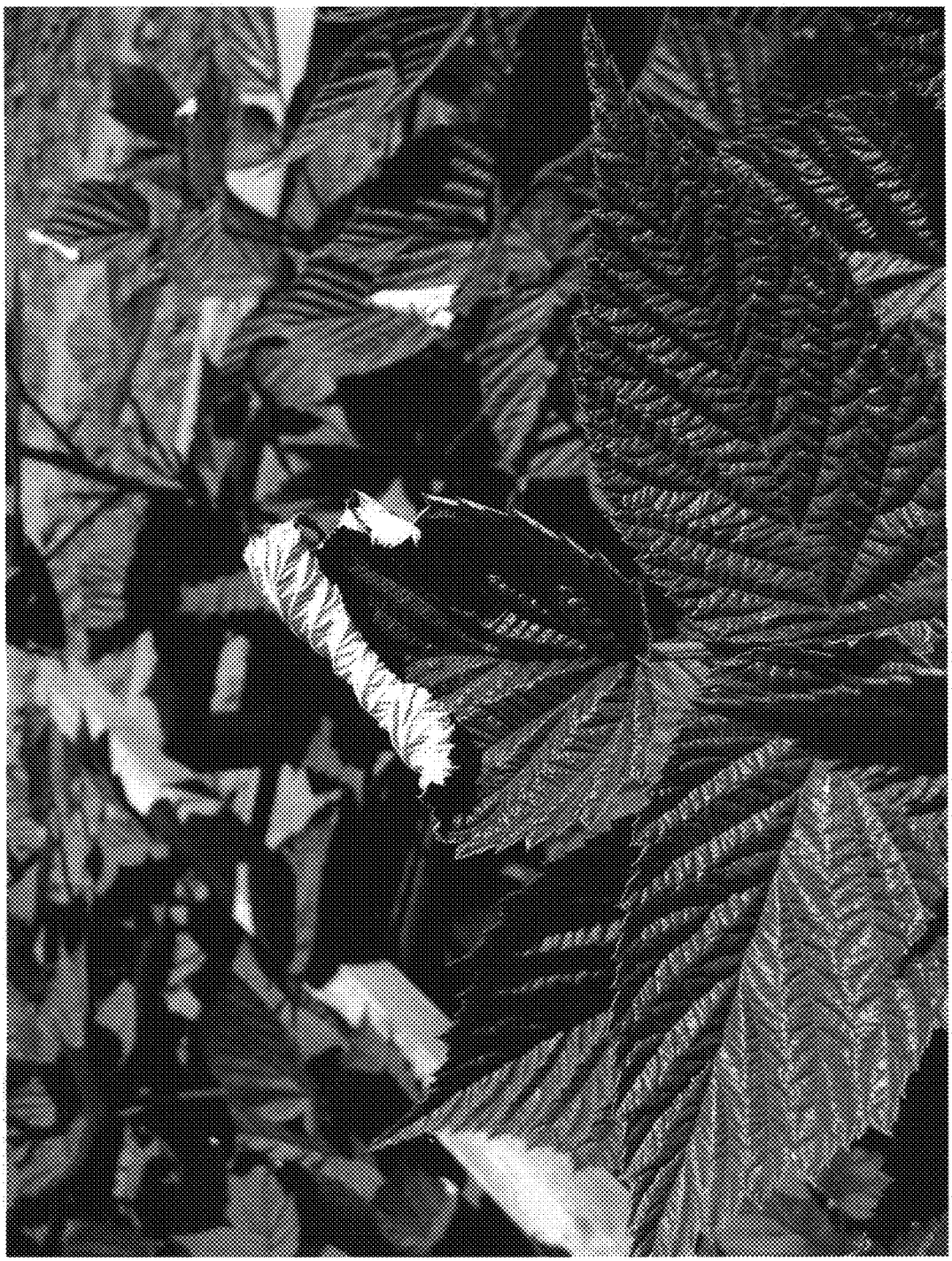
FIG. 3 is a close-up photograph showing ripe and unripe fruit and leaf detail on laterals of the Raspberry cultivar 'Pacific Gema'.
Figure 4:
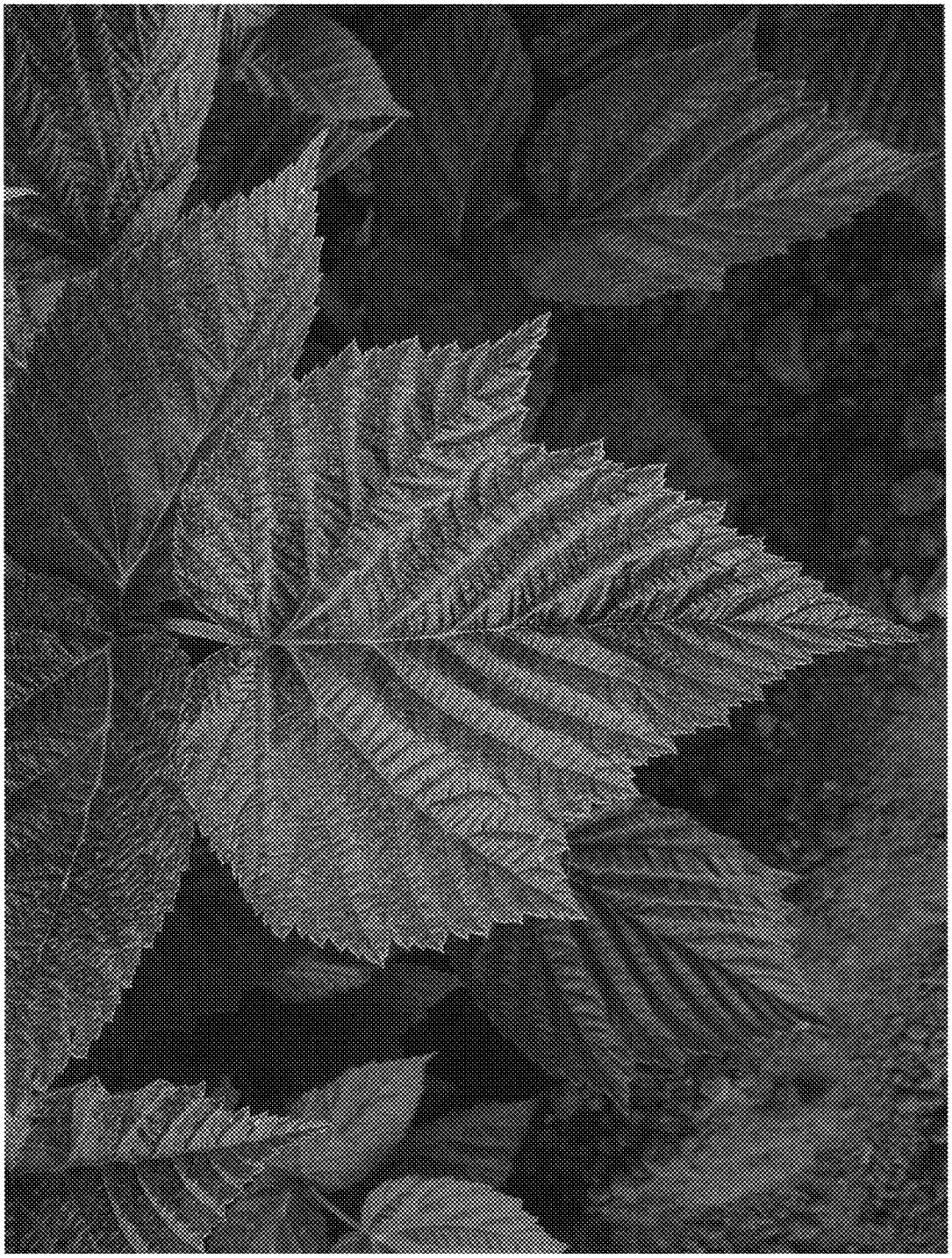
FIG. 4 is a further close-up photograph showing ripe and unripe fruit and leaf detail of the Raspberry cultivar 'Pacific Gema'.
Figure 5:
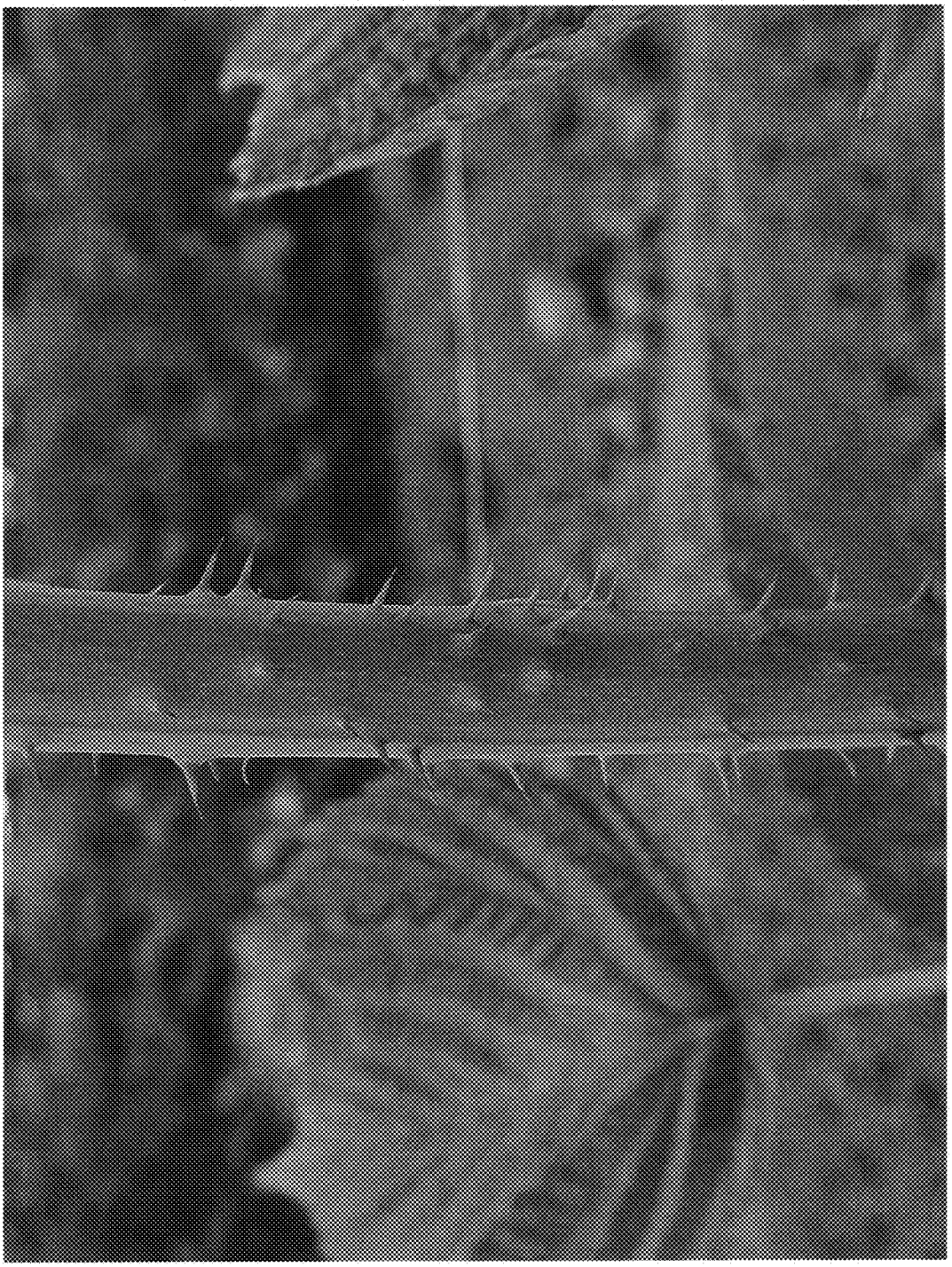
FIG. 5 is a photograph showing the lightly pigmented spines that are typical of the raspberry cultivar 'Pacific Gema'.

Note: statements of characteristics herein represent exemplary observations of the cultivar herein and will vary depending on time of year, location, annual weather, etc.

Cultivar name: 'Pacific Gema'.

Classification:

*Family*.—Rosaceae.

*Botanical name*.—*Rubus idaeus* L.

*Common name*.—Raspberry.

Parentage:

*Female parent*.—'Pacific Deluxe'.

*Male parent*.—'414a'. In contrast to the unpatented male parent '414a', the present invention is significantly larger in fruit size, greater in vigor and has reduced pubescence on the drupelets, resulting in a glossier appearance in fruits of 'Pacific Gema'. 'Pacific Gema' was first identified in a field with other seedlings in May 2010 at Watsonville, Calif. USA. The field had been planted in 2009 among other seedlings generated from hand-pollinated crosses performed in 2008. 'Pacific Gema' was first propagated asexually by crown division in August 2010 in Watsonville, Calif. USA. The crown on the original plant was dug and parted into basal cane pieces (approximately 15 cm long) with root attached and replanted into a selection plot elsewhere on the farm, resulting in a 3-fold increase. In September 2011, two actively growing primocanes were dug (with root attached) and shipped to Lafayette, Oreg. USA, where vegetative material was explanted and established in vitro for micropropagation.

Growing location for the observations herein: Watsonville, Calif. USA.

Time of year (season): Early and late summer for floricanes and primocanes, respectively.

Age of plants used for this discussion: Crown age of about 4.5 years and a cane age of about 4-8 months.

Age of plants used for the photographs in the figures: Crown age of about 4.5 years and a cane age of about 8 months.

Type of greenhouse covering or growing structure, or field: High tunnel over field.

Light: Natural.

References to color refer to the The Royal Horticultural Society Colour Chart—Fifth Edition ("R.H.S.").

Observations for floricanes herein were made in June 2013. Observations for primocanes herein were made in August 2013.

Plant:

*Form/shape*.—Vase.

*Growth habit*.—Erect.

*Height*.—1.2 m as measured from base.

*Spread*.—0.6 m as measured from terminal leaflet tip to terminal leaflet tip.

*Propagation methods*.—Division.

*Time to initiate and develop roots*.—24 days.

*Root description*.—Fibrous.

Primocanes:

*Cane diameter*.—Base: 1.15 cm|Middle: 1.0 cm|Tip: 0.3 cm.

*Cane length*.—2.1 m.

*Number of node per cane*.—40-43.

*Internode length*.—Base: 2.25-4 cm|Middle: 1.75-4 cm|Tip: 1.5-1.75 cm.

*Number of canes/hill*.—5-7.

*Cane color*.—Undertone: RHS 145B. Overtone: RHS 186A.

*Spines*.—Present. Spine density: Base: 5-7/$cm^2$|Middle: 2-3/$cm^2$|Tip: 1/$cm^2$. Spine shape: Acute. Spine length: 0.1 cm. Spine width: 0.01 cm. Spine apex descriptor: Acute. Spine color: RHS 186B.

*Vegetative bud shape*.—Acute.

*Vegetative bud length*.—0.55 cm.

*Vegetative bud diameter* (*base*).—0.3 cm.

*Vegetative bud diameter* (*tip*).—0.1 cm.

*Vegetative bud color*.—RHS 166A.

*Reproductive bud shape* (*base/tip*).—Truncate/acuminate.

*Reproductive bud length*.—1.3 cm.

*Reproductive bud diameter* (*base*).—0.89 cm.

*Reproductive bud diameter* (*tip*).—0.09 cm.

*Reproductive bud color*.—RHS 144A.

*Reproductive bud texture*.—Pubescent.

Floricanes:

*Cane diameter*.—Base: 1.5 cm|Middle: 1.2 cm|Tip: 1.1 cm.

*Cane length*.—1.1-1.2 m.

*Number of nodes per cane*.—13-16. Internode Length: 11.4 cm|17.1 cm|13.9 cm.

*Cane color*.—Lower Cane: RHS 199D. Upper Cane: RHS 165B.

*Spines*.—Present. Spine density: Base: 5-7/$cm^2$|Middle: 2-3/$cm^2$|Tip: 1/$cm^2$. Spine shape: Acute. Spine length: 0.1 cm. Spine width: 0.1 cm. Spine apex descriptor: Acute. Spine color: RHS 186B.

*Vegetative bud shape*.—Acute.

*Vegetative bud length*.—0.55 cm.

*Vegetative bud diameter* (*base*).—0.3 cm.

*Vegetative bud diameter* (*tip*).—0.1 cm.

*Vegetative bud color*.—RHS 166A.

*Reproductive bud shape* (*base/tip*).—Truncate/acuminate.

*Reproductive bud length*.—1.3 cm.

*Reproductive bud diameter* (*base*).—0.89 cm.

*Reproductive bud diameter* (*tip*).—0.09 cm.

*Reproductive bud color*.—RHS 144A.

*Reproductive bud texture*.—Pubescent.

*Winter hardiness*.—Unknown outside of USDA Hardiness Zone 9b (Watsonville, Calif.). This cultivar is best adapted to the mild coastal conditions of California.

*Drought/heat tolerance*.—Leaf tips of 'Pacific Gema' will characteristically burn under high temperature conditions. Pollen viability and fruit quality of raspberry generally begins to decline above 30° C. This is consistent with observations of 'Pacific Gema'. Raspberries are generally not drought tolerant, and 'Pacific Gema' has not been tested in unirrigated plots.

Leaves:

*Complete leaf*.—Length: 12.1-18.4 cm. Width: 7.6-11.4 cm. Number of leaflets: 3-5.

*Terminal leaflet*.—Size: Length (cm): 12.1 cm. Width (cm): 10.2 cm. Length/Width ratio: 1.2. Leaf shape of apex: Acuminate. Leaf shape of base: Cordate. Leaf margin: Doubly Serrate. Leaf texture: Moderate Interveinal Puckering. Number of serrations per leaf: 98 -129. Leaf shape of serrations: Flexuous-Flexuous. Leaf color: Upper Surface: RHS 136A. Lower Surface: RHS 136D. Leaf venation pattern: Reticulate. Leaf venation color: Upper surface: RHS 144A. Lower surface: RHS 145C. Leaf pubescence density: None. Color of leaf pubescence: N/A. Shape of leaf in cross-section: Simple Cordate. Number of leaflets/leaf: Primocane: 3. Floricane: 3-5. Interveinal blistering within leaf: Moderate. Leaf glossiness: Low.

*Primocane leaves*.—Petiole length: 6.0 cm. Petiole diameter: 0.2 cm. Petiole Color: Upper: RHS 143C. Lower: RHS N144C. Rachis length: 3.3 cm. Stipule length: 0.7 cm. Stipules per leaf: 2. Stipule Width: 0.1 cm. Stipule Color: RHS N144D. Color: Upper Surface: RHS 136A. Lower Surface: RHS 136D.

*Terminal leaflet*.—Length: 12.1 cm. Width: 8.9 cm. Rachis length: 3.3 cm.

*Distal lateral leaflet*.—Not Present. Length: N/A. Width: N/A. Petiolule length: N/A.

*Basal lateral leaflet*.—Length: 9.5 cm. Width: 6.4 cm. Petiolule length: 0.1 cm.

*Floricane leaves*.—Petiole length: 5.4 cm. Stipule length: 0.7 cm. Stipules per leaf: 2. Stipule Width: 0.1 cm. Stipule Color: RHS N144D. Color Upper surface: RHS 137A. Lower surface: RHS 191B.

*Terminal leaflet*.—Length: 9.5 cm. Width: 7.0 cm. Rachis length: 1.6 cm. Distal lateral leaflet: Not Present. Length: N/A. Width: N/A.

*Petiolule*.—Length: N/A. Diameter: N/A. Color: N/A.

*Basal lateral leaflet*.—Length: 6.4 cm. Width: 4.4 cm.

*Petiolule*.—Length: 0.1 cm. Diameter: 0.1 cm. Color: Upper: RHS 143C. Lower: N144C.

Flowers:

*Time of flowering* (50% *of plants at first flower*).—June 20 on primocanes, April 2 on floricanes.

*Flower size*.—Length: 0.6 cm. Diameter: 0.9 cm.

*Fragrance*.—None.

*Peduncle*.—Length: 0.6 cm. Diameter: 0.05 cm. Color: RHS 138B. Pubescence: Present. Texture: Smooth.

*Perianth*.—Flowering trusses shape: Truncate.

*Petals*.—Color (upper and lower): RHS 155C. Number per flower: 5. Shape: Oblanceolate. Length: 0.6 cm. Width: 0.2 cm. Apex descriptor: Obtuse. Base Descriptor: Truncate. Margin descriptor: Smooth with some undulations. Texture: Smooth with visible striations.

*Sepals*.—Quantity: 5. Length: 1.1 cm. Width: Base: 0.4 cm|Mid: 0.2 cm|Tip: 0.01 cm. Color: RHS 139C. Apex descriptor: Acute. Margin descriptor: Smooth. Texture: Pubescent.

*Pedicel*.—Color: RHS 144A. Length: 2.8 cm. Diameter: 0.1 cm.

Reproductive organs: Self-fertile: yes.

*Male*.—Stamen Number: 98. Filament: Length: 0.2 cm. Diameter: 0.01 cm. Color: RHS 157C. Anther: Length: 0.07 cm. Diameter: 0.05 cm. Color: RHS 162D. Pollen: Color: RHS 162D. Amount: Heavy.

*Female*.—Style: Length: 0.1 cm. Diameter: 0.01 cm. Color: RHS 157D. Stigma: Length: 0.01 cm. Diameter: 0.01 cm. Color: RHS 157D. Ovary: Length: 0.1 cm. Diameter: 0.071 cm. Color: N144D.

Fruit:

*Predominant shape*.—Conical.

*Weight* (*g*).—4.5 g.

*Length*.—2.5 cm.

*Width*.—1.5 cm.

*Length/width ratio*.—1.7.

*Receptacle*.—Length: 1.8 cm. Diameter: Base: 0.6 cm|Mid: 0.3 cm|Tip: 0.05 cm. Color: RHS 9D.

*Drupelet*.—Length: 0.4 cm. Diameter: 0.2 cm. Number: 103. Weight: 0.2 g.

*Fruit color*.—External: RHS 46A. Internal: RHS 185B.

*Firmness of skin*.—Moderately firm.

*Firmness of flesh*.—Moderately firm.

*Hollow center*.—Present.

*Number of fruit per node*.—2-4.

*Time of ripening* (50% *of plants with first fruit*).—July 28 on primocanes in a first-year planting. May 25 on floricanes.

*Time of fruiting*.—Late spring on floricanes, late summer and early autumn on primocanes.

*Type of bearing*.—Remontant.

*Fruit yield*.—24,244 lb/a/cycle.

*Average brix*.—9.44.

Typical market use: Fresh.

Keeping quality: Excellent.

Shipping quality: Very good.

Pest and disease resistance: Plants of 'Pacific Gema' have exhibited high field tolerance to *Phytophthora rubi, Phragmidium rubi-idaei*, and field tolerance to Raspberly Bushy Dwarf Virus (RBDV).

What is claimed is:

1. A new and distinct cultivar of Raspberry plant named 'Pacific Gema' as described and shown herein.

* * * * *